United States Patent [19]

Ernhoffer et al.

[11] Patent Number: 5,171,861

[45] Date of Patent: Dec. 15, 1992

[54] THIADIAZOLE-ARYL SULFONATE REACTION PRODUCTS AS MULTIFUNCTIONAL ADDITIVES AND COMPOSITIONS CONTAINING SAME

[75] Inventors: Robert E. Ernhoffer, Sewell; Arjun K. Goyal, Woodbury; Andrew G. Horodysky, Cherry Hill, all of N.J.; Derek A. Law, Yardley, Pa.; Shi-Ming Wu, Newtown, Pa.

[73] Assignee: Mobil Oil Corporation, Fairfax, Va.

[21] Appl. No.: 605,197

[22] Filed: Oct. 29, 1990

[51] Int. Cl.$^5$ ............... G07D 285/125; C10M 135/36
[52] U.S. Cl. .................................. 548/142; 252/47.5; 548/106; 548/126; 548/127; 548/135
[58] Field of Search ............... 548/142, 106, 126, 127, 548/135; 252/47.5

[56] References Cited

U.S. PATENT DOCUMENTS 2,736,729  2/1956  Krzikalla ............... 548/142
4,357,159  11/1982  Gloor ................... 560/307

FOREIGN PATENT DOCUMENTS 57-147627  9/1982  Japan.

OTHER PUBLICATIONS

Sanecki, Chem. Ab. 101, 37947v 1984.
Anwar Chem. Ab. 96 122697k 1982.

Primary Examiner—Robert Gerstl
Attorney, Agent, or Firm—Alexander J. McKillop; Charles J. Speciale; Howard M. Flournoy

[57] ABSTRACT

Dimercaptothiadiazole reacted with arylsulfonic acids preformed or formed in situ in lubricants provide multifunctional antioxidant, antiwear, and corrosion inhibiting properties thereto.

36 Claims, No Drawings

THIADIAZOLE-ARYL SULFONATE REACTION PRODUCTS AS MULTIFUNCTIONAL ADDITIVES AND COMPOSITIONS CONTAINING SAME

BACKGROUND OF THE INVENTION

This application is directed to the use of additive concentrations of neutralized and/or acidified metallic hydrocarbyl sulfonate/mercaptothiazole reaction products and lubricant compositions containing same.

Metallic aryl sulfonates such as calcium dinonylnaphthalene sulfonates have been widely used in petroleum and synthetic lubricants as rust and corrosion inhibiting additives. Additionally, these and related metallic aryl sulfonates have, on occasion, provided good detergency and demulsibility properties in a variety of lubricant formulations.

Various reaction products of mercapto- and dimercaptothiadiazoles have been known to possess extreme pressure/antiwear properties, as exemplified in U.S. Pat. No. 4,661,273; 4,382,869; and 4,678,592.

Accordingly, the use of metallic aryl sulfonates as rust inhibitor, corrosion inhibitor, and/or demulsifier additives in lubricants and greases is well known as is the use of mercapto- and dimercaptothiadiazoles for their extreme pressure/antiwear properties.

Lubricants in service applications often generate acid species or acid-forming species, especially when exposed to high operating temperatures, extended service life and/or contact with atmospheric oxygen during aeration caused by churning or moving elements of the lubricated machine. Acid-forming species can also be formed via hydrolysis or other similar mechanisms.

If metallic aryl sulfonates are used as additives in such systems described above, neutralization or acidification to form sulfonic acids can occur. If both metallic aryl sulfonates and dimercaptothiadiazole are used together in a lubricant, or alternatively pre-reacted in the presence of small quantities of organic or inorganic acids, the resulting products exhibit excellent lubricating properties in conjunction with good antioxidant, antiwear, antirust, and corrosion inhibiting performance, with potential antifatigue, cleanliness, thermal stabilizing and/or friction modifying properties.

The use of reaction products of acidified sulfonates and dimercaptothiadiazoles as multifunctional additives has not been reported in any literature known to applicants and is, therefore, believed to be novel. The composition of matter, the lubricant compositions containing such additives, and the use of such reaction products in lubricants to improve the performance properties are all believed to be unique and heretofore unknown.

SUMMARY OF THE INVENTION

Improved lubricant compositions are provided by incorporating into suitable hydrocarbyl lubricants or functional fluids additive quantities of the reaction products of mercaptothiadiazoles and hydrocarbyl sulfonic acids or acid generating species. The product of the sulfonic acid or derivative thereof and the mercaptothiadiazole may be preformed or formed in situ.

An object of the invention is to provide lubricant compositions having improved multifunctional antioxidant, antiwear and corrosion inhibiting characteristics. To achieve this objective, this patent application discloses a unique additive composition made by the reaction of at least partially neutralized or acidified sulfonates with mercaptothiadiazoles and their use in lubricants.

DESCRIPTION OF PREFERRED EMBODIMENTS

Metallic hydrocarbyl aryl sulfonates can be neutralized in service, in situ, or via addition of small quantities of organic or inorganic acids, as shown below:

$$ArSO_3M + H^+ \rightarrow ArSO_3H$$

Where Ar is dialkylnaphthalene, or dihydrocarbylarene and wherein hydrocarbyl is selected from the group consisting of alkyl, alkaryl, arylalkyl or is cyclic and is preferably $C_1$ to about $C_{30}$ alkyl and M is alkali or alkaline-earth metal and/or a nitrogenous group such as amine or ammonium and preferably sodium, calcium, zinc, or barium. Especially preferred sulfonates are sodium or calcium nonylnaphthalene. The above acid can then react in service or in situ with mercaptothiadiazoles to form multifunctional additives with enhanced antioxidant, antiwear, and rust/corrosion inhibiting properties.

Any appropriate mercaptothiadiazoles may be used herein. Some suitable thiadiazoles include but are not limited to:

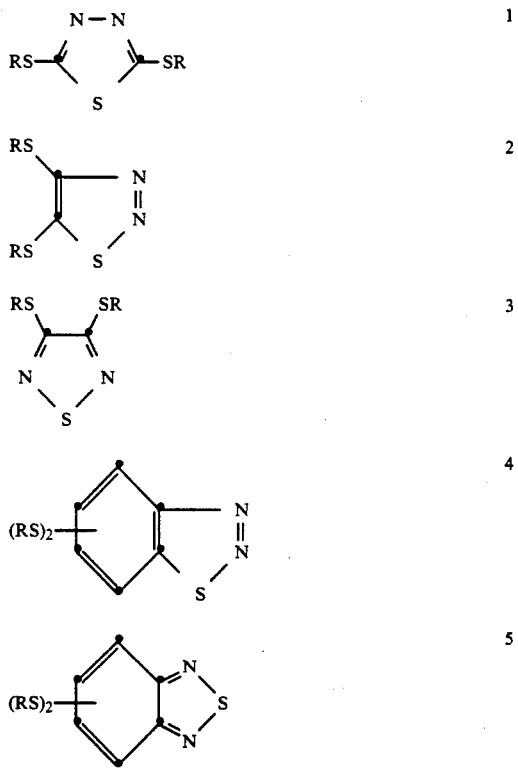

In the above general structures (1 to 6), R may include hydrogen and $C_1$ to $C_{30}$ hydrocarbyl, and at least one free mercapto group. Preferred is 2,5-dimercapto-1,3,4-thiadiazole (1 where R=H), however, any appropriate mercapto-thiadiazole may be used herein. Some suitable examples include but are not limited to 3,4-dimercapto-1,2,5-thiadiazole, 4,5-dimercapto-1,2,3-thiadiazole, 4,7-dimercaptobenzo-1,2,3-thiadiazole, 4,5-dimercaptobenzo-2,1,3-thiadiazole, 4,6-dimercaptobenzo-2,1,3-thiadiazole, 5,6-dimercaptobenzo-2,1,3- thiadiazole, 5,7-dimercaptobenzo-2,1,3-thiadiazole, 6,7-dimercaptobenzo-2,1,3-thiadiazole.

Reaction conditions can vary widely from temperatures of about 50° C. to about 250° C. or reflux, pressures from ambient or atmospheric to slightly higher if desired. Reaction times may also vary widely depending upon specific reagents, temperature and pressure and if a solvent is used. Generally the reaction time varies from about 3-4 to 12 hrs or more. Any suitable hydrocarbon solvent such as toluene or xylene or mixed xylenes may be used. An excess of one reagent or another can be used. Nevertheless, molar quantities, less than molar quantities or more than molar quantities may be used. Preferred, however, are molar quantities of sulfonate to thiadiazole of from about 10:1 to about 1:2.

In preparing a lubricant composition the additive is added to the base lubricating oil stock in a concentration of between 0.01 and 10 percent by weight of the total composition and preferably from about 0.1 to about 5 percent. In general, the mineral oils, both paraffinic, naphthenic and mixtures thereof, employed as a lubricating oil or as the grease vehicle, can be of any suitable lubricating viscosity range, as for example, from about 45 SSU at 100° F. to about 6000 SSU at 100° F. and preferably from about 50 to about 250 SSU at 210° F. These oils may have viscosity indexes ranging to 100 or higher. Viscosity indexes from about 70 to about 95 are preferred. The average molecular weight of these oils can range from about 250 to about 800.

Where the lubricant is employed as a grease, the lubricating oil is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt and dissolve when used at the required temperature within a particular environment; however, in all other respects, any material which is normally employed for thickening or gelling hydrocarbon fluids for forming grease and be used in preparing the aforementioned improved grease in accordance with the present invention.

In instances where synthetic oils, or synthetic oils employed as the vehicle for the grease, are desired in preference to minerals oils, or in preference to mixtures of mineral and synthetic oils, various synthetic oils may be utilized successfully. Typical synthetic oil vehicles include polyisobutylenes, polybutenes, hydrogenated polydecenes, polypropylene glycol, polyethylene glycol trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted diphenyl ethers typified by a butyl-substituted bis(p-phenoxy phenyl) ether, and phenoxy phenylethers.

It is to be understood that the lubricant compositions described herein can also contain other materials, e.g., corrosion inhibitors, extreme pressure agents, viscosity index improvers, antioxidants, antiwear agents and the like can be used. These include, but are not limited to, phenates, sulfonates, succinimides, zinc dialkyl or diaryl dithiophosphates, and the like.

The following examples are illustrative only and are not intended as limitations:

EXAMPLE 1

Approximately 193 g(0.2 mol) of sodium dinonylnaphthalene sulfonate (commercially obtained from King Industries, Inc. as Nasul SS) and 100 ml of toluene were charged to a stirred reactor equipped with a thermometer, condenser, nitrogen sparger, and agitator and acidified with 16 ml of 30% sulfuric acid. The mixture was stirred for one hour at 60° C. before addition of 2,5-dimercapto-1,3,4-thiadiazole (15 g, 0.1 mol) in one portion and then was heated to reflux for three hours. The resulting reaction mixture was filtered; the filtrate was further washed with water (2×50 ml) and evaporated under a pressure at 130° C. to yield 190 g of grayish brown fluid.

EXAMPLE 2

Under the same reaction conditions as described in Example 1, approximately 192 g(0.1 mol) of calcium dinonylnaphthalene sulfonate (commercially obtained from King Industries, Inc. as Nasul 729) in 100 ml of toluene was acidified with 8 ml of 30% sulfuric acid. The mixture was stirred for one hour at 60° C., then further reacted with 2,5-dimercapto-1,3,4-thiadiazole (15 g, 0.1 mol) for three hours at reflux. 200 g of dark brown fluid was obtained as the final product calcium or barium.

Evaluation of Product

The products of the examples were evaluated by Catalytic Oxidation Test (Table 1) and Four-Ball Wear Test (Table 2). The results demonstrate the remarkable antioxidant features of the examples with respect to control of increase in viscosity and acidity, as well as good antiwear activities.

Catalytic Oxidation Test

Basically, the test lubricant is subjected to a stream of air which is bubbled through at the rate of five liters per hour respectively at 325° F. for 72 hours. Present in the composition are samples of metals commonly used in engine construction, namely, iron, copper, aluminum, and lead. See U.S. Pat. No. 3,682,980, incorporated herein by reference for further details of the test.

TABLE I

| Viscosity Item | Catalytic Oxidation Test 325° F., 72 hours | |
|---|---|---|
| | Change in Acid Number TAN | Percent Change in Kinematic KV % |
| Base Oil (100% solvent paraffinic neutral mineral oil) | 8.16 | 110.0 |
| Base Oil plus 1% of Example 1 | 2.60 | 19.6 |
| Base Oil plus 1% of Example 2 | 0.85 | 7.1 |

Four-Ball Wear Test

Three stationary balls are placed in the lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes.

TABLE 2

| Four-Ball Wear Test (60 kg load, 200° F., 2000 rpm, 30 min) | |
|---|---|
| Item | Wear Scar Diameter, mm |
| Base Oil (80% solvent paraffinic bright, 20% solvent paraffinic neutral mineral oils) | 3.94 |
| Base Oil plus 1% of Example 1 | 0.84 |
| Base Oil plus 1% of Example 2 | 2.16 |

The above data clearly document that the use of additive concentrations of neutralized and/or acidified metallic hydrocarbyl sulfonate/mercaptothiadiazole reaction products in premium quality industrial, automotive, marine lubricants and greases will provide multifunctional antiwear/antioxidant/corrosion inhibiting properties thereto.

We claim:

1. A reaction product suitable for use as a multifunctional lubricant additive obtained by reacting an acidified or neutralized metallic hydrocarbyl sulfonate, described by the following formula:

ArSO$_3$M where Ar is or dihydrocarbylarene and hydrocarbyl is C$_1$ to about C$_{30}$ wherein hydrocarbyl is selected from the group consisting of alkyl, alkaryl, arylalkyl is cyclic and M is an alkali or alkaline-earth metal or a nitrogenous group, with a mercaptothiadiazole at temperatures varying from about 50° C. to about 250° C. or reflux, pressures varying from ambient to slightly higher in molar ratios of sulfonate to mercaptothiadiazole of from about 10:1 to about 1:2 for a time, varying from about 3 to about 12 hours or more, sufficient to obtain the desired metallic hydrocarbyl sulfonate/mercaptothiadiazole reaction product having improved multifunctional antioxidant, antiwear, rust/corrosion inhibiting, and demulsifying properties.

2. The reaction product of claim 1 where Ar is dialkylnaphthalene.

3. The reaction product of claim 1 where the metallic hydrocarbyl sulfonate is acidified or neutralized in situ or via addition of organic or inorganic acid.

4. The product of claim 1 where the metal is selected from barium, calcium, zinc or sodium.

5. The product of claim 4 where the metal is calcium.

6. The product of claim 4 where the metal is sodium.

7. The product of claim 1 where the nitrogenous group is an amine or ammonium group.

8. The product of claim 1 where the mercaptothiadiazole is selected from at least one of the structures described below.

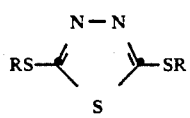

1

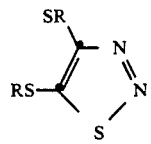

2

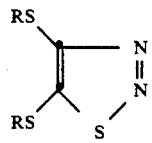

3

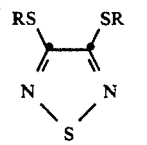

4

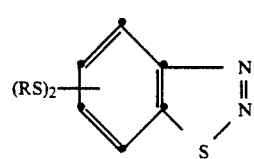

5

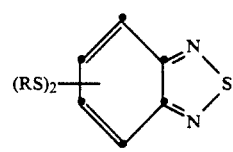

6 where R is hydrogen, C$_1$ to about C$_{30}$ hydrocarbyl and having at least one free mercapto group.

9. The product of claim 1 where the reactants are sodium dinonylnaphthalene sulfonate and 2,5-dimercapto-1,3,4-thiadiazole.

10. The product of claim 1 where the reactants are calcium dinonylnaphthalene sulfonate and 2,5-dimercapto-1,3,4-thiadiazole.

11. A process of making a compound highly suitable for use as a multifunctional lubricant additive comprising reacting an acidified or neutralized metallic hydrocarbyl sulfonate, described by the following formula:

ArSO$_3$M where Ar is dihydrocarbylarene and hydrocarbyl is C$_1$ to about C$_{30}$ wherein hydrocarbyl is selected from the group consisting of alkyl, alkaryl, arylalkyl or cyclic and M is an alkali or alkaline-earth metal or a nitrogenous group, with a mercaptothiadiazole at temperatures varying from about 50° C. to about 250° C. or reflux, pressures varying from ambient to slightly higher in molar ratios of sulfonate to mercaptothiadiazole varying from about 10:1 to about 1:2 for a time sufficient to obtain the desired metallic hydrocarbyl sulfonate/mercaptothiadiazole reaction product having improved multifunctional antioxidant, antiwear, rust/corrosion inhibiting, and demulsifying properties.

12. The process of claim 11 where Ar is dialkylnaphthalene.

13. The process of claim 11 where the metallic hydrocarbyl sulfonate is acidified or neutralized in situ or via addition of organic or inorganic acid.

14. The process of claim 11 wherein the metal is selected from barium, calcium, zinc or sodium.

15. The process of claim 14 where the metal is calcium.

16. The process of claim 14 where the metal is sodium.

17. The process of claim 11 where the nitrogenous group is an amine or ammonium group.

18. The process of claim 11 where the mercaptothiadiazole is selected from at least one of the structures described below.

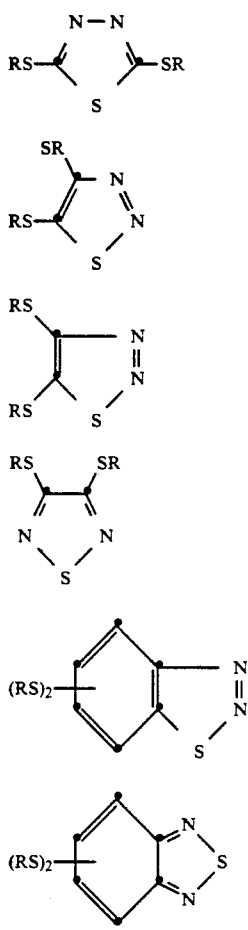

where R is hydrogen, $C_1$ to about $C_{30}$ hydrocarbyl and having at least one free mercapto group.

19. The process of claim 11 where the reactants are sodium dinonylnaphthalene sulfonate and 2,5-dimercapto-1,3,4-thiadiazole.

20. The process of claim 11 where the reactants are calcium dinonylnaphthalene sulfonate and 2,5-dimercapto-1,3,4-thiadiazole.

21. A lubricant composition having improved multifunctional antioxidant/antiwear/rust-corrosion inhibiting properties comprising a major proportion of an oil of lubricating viscosity or a grease prepared therefrom and a minor proportion of additive product of reaction obtained by reacting an acidified or neutralized metallic hydrocarbyl sulfonate, described by the following formula:

$ArSO_3M$ where Ar is dihydrocarbylarene and hydrocarbyl is $C_1$ to about $C_{30}$ wherein hydrocarbyl is selected from the group consisting of alkyl, alkaryl, arylalkyl or cyclic and M is an alkali or alkaline-earth metal or a nitrogenous group, with a mercaptothiadiazole at temperatures varying from about 50° C. to about 250° C. or reflux, pressures varying from ambient to slightly higher in molar ratios of sulfonate to mercaptothiadiazole of from about 10:1 to about 1:2 for a time, varying from about 3 to about 12 hours or more, sufficient to obtain the desired metallic hydrocarbyl sulfonate/mercaptothiadiazole reaction product having improved multifunctional antioxidant, antiwear, rust/corrosion inhibiting, and demulsifying properties.

22. The composition of claim 21 where Ar is dialkylnaphthalene.

23. The composition of claim 21 where the metallic hydrocarbyl sulfonate is acidified or neutralized in situ or via addition of organic or inorganic acid.

24. The composition of claim 21 where the metal is selected from barium, calcium, zinc or sodium.

25. The composition of claim 24 where the metal is calcium.

26. The composition of claim 24 where the metal is sodium.

27. The composition of claim 21 where the nitrogenous group is an amine or ammonium group.

28. The composition of claim 21 where the mercaptothiadiazole is selected from at least one of the structures described below.

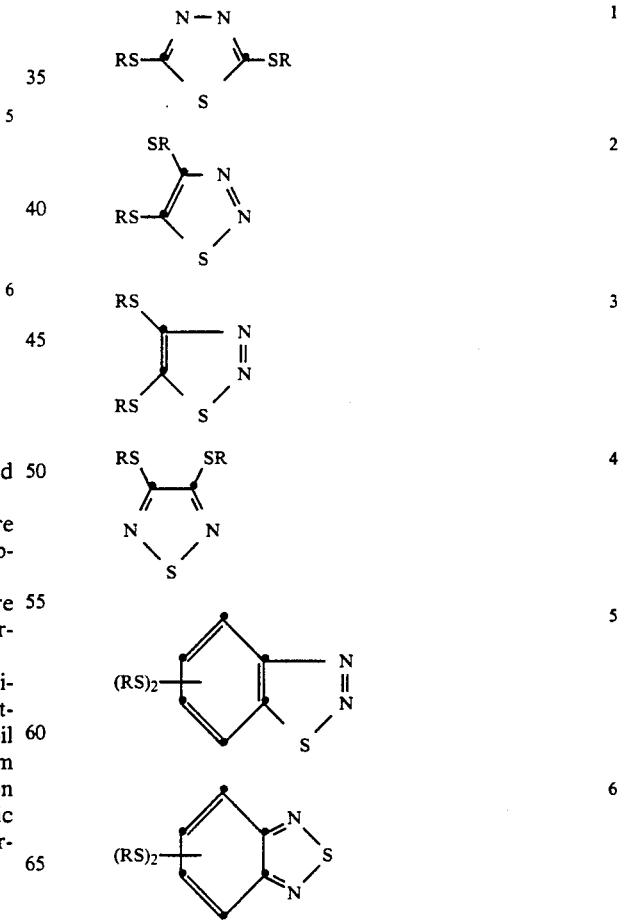

where R is hydrogen, $C_1$ to about $C_{30}$ hydrocarbyl and having at least one free mercapto group.

29. The composition of claim 21 where the reactants are sodium dinonylnaphthalene sulfonate and 2,5-dimercapto-1,3,4-thiadiazoles.

30. The composition of claim 21 where the reactants are calcium dinonylnaphthalene sulfonate and 2,5-dimercapto-1,3,4-thiadiazole.

31. The composition of claim 21 where said oil of lubricating viscosity is selected from (1) mineral oils, (2) synthetic oils, (3) mixtures of (1) and (2) or is a grease prepared from any one of (1), (2) or (3).

32. The composition of claim 31 where said oil is (1) a mineral oil.

33. The composition of claim 31 where said oil is (2) a synthetic oil.

34. The composition of claim 31 where the lubricant is a grease.

35. A method of improving the antioxidant, antiwear, rust/corrosion inhibiting and demulsifying characteristics of a lubricant composition comprising an oil of lubricating viscosity or grease prepared therefrom comprising adding thereto from about 0.01 to about 10 wt% of an additive product of reaction obtained by reacting an acidified or neutralized metallic hydrocarbyl sulfonate described by the following formula:

$$ArSO_3M$$

where Ar is dihydrocarbylarene or $C_1$ to about $C_{30}$ hydrocarbyl selected from alkyl, alkaryl, arylalkyl or cyclic and M is alkali or alkaline-earth metal or a nitrogenous group and a mercaptothiadiazole at temperatures varying from about 50° C. to about 250° C. or reflux, pressures varying from ambient to slightly higher in molar ratios of sulfonate to thiadiazole of from about 10:1 to about 1:2 for a time sufficient to obtain the desired metallic hydrocarbyl sulfonate/mercaptothiadiazole reaction product having improved multifunctional antioxidant, antiwear, rust/corrosion inhibiting, and demulsifying properties.

36. The method of claim 35 wherein the additive product of reactants comprises from about 0.1 to about 5 wt %.

* * * * *